United States Patent [19]

Bewick

[11] Patent Number: 5,256,627
[45] Date of Patent: Oct. 26, 1993

[54] USE OF MICROORGANISM TO PRODUCE TOXIN

[75] Inventor: Thomas A. Bewick, Gainesville, Fla.

[73] Assignee: University of Florida, Gainesville, Fla.

[21] Appl. No.: 720,098

[22] Filed: Jun. 24, 1991

Related U.S. Application Data

[63] Continuation-in-part of Ser. No. 278,685, Dec. 1, 1988, abandoned.

[51] Int. Cl.$^5$ ............................................. A01N 63/04
[52] U.S. Cl. ..................................... 504/117; 504/118
[58] Field of Search ........................ 71/65, 79; 504/117

[56] References Cited

U.S. PATENT DOCUMENTS

| | | | |
|---|---|---|---|
| 3,849,104 | 11/1974 | Daniel et al. | 71/65 |
| 3,999,973 | 12/1976 | Templeton | 71/79 |
| 4,097,261 | 6/1978 | Conway et al. | 71/66 |
| 4,162,912 | 7/1979 | Charudattan | 71/79 |
| 4,390,360 | 6/1983 | Walker | 71/79 |
| 4,419,120 | 12/1983 | Walker | 71/79 |
| 4,626,271 | 12/1986 | Gleason | 71/66 |
| 4,776,873 | 10/1988 | Caulder et al. | 71/92 |
| 4,915,726 | 4/1990 | Bewick et al. | 71/79 |

OTHER PUBLICATIONS

Blaney, C. L. et al. "Fungal Pathogens with Potential for Biocentral of Yellow Nutsedge" J. Elisha Mitchell Sci. Soc. 103(2), 1987, pp. 71–76; as abstracted by Biosis 88:478267.
Nitzani, E. et al. "Foliar Diseases of Purple Nutsedge . . . ", Phytoparasitica 18(3), 1990, pp. 240–241; as abstracted by Biosis 91:43052.
Tsuda, M. et al. "Sexuality for the Telemorph . . . ", Trans. Mycol. Soc. Jpn. 26(1), 1985, pp. 27–40; as abstracted by Biosis 85:431754.
Roy, A. K. et al. "Aflatoxin Problems in Some Medicinal Plants . . . " Int. J. Crude Drug Res., 1989, 27(3), pp. 156–160; as abstracted by Chemical Abstracts 112:104648Q.
Charudattan, R. et al. "Biological Control of Weeds with Plant Pathogens", John Wiley & Sons, New York, 1982, pp. 237–238.
McWhorter, C. G. (1984) "Future Needs in Weed Science," Weed Science 32:850–855.
Pereira, W., G. Crabtree, R. D. William (1987) "Herbicide Action on Purple and Yellow Nutsedge (*Cyperus rotundus* and *C. esculentus*)," Weed Technology 1:92–98.
Weisskopf, M. (1988) "A Pesticide Peril in a Land of Plenty," The Washington Post Weekly Edition 5(47):10–11, Washington, D.C.
Fleming, M. H. (1987) "Agricultural Chemicals in Ground Water: Preventing Contamination by Removing Barriers Against Low-Input Farm Management," Amer. J. Alternative Agriculture 2:124–130.
Phatak, S. C., M. B. Callaway, C. S. Vavrina (1987) "Biological Control and Its Integration in Weed Management Systems for Purple and Yellow Nutsedge (*Cyperus rotundus* and *C. esculentus*)," Weed Technology 1:94–91.

Primary Examiner—Allen J. Robinson
Assistant Examiner—John D. Pak
Attorney, Agent, or Firm—Saliwanchik & Saliwanchik

[57] ABSTRACT

The subject invention relates to a novel means of producing a toxin. The subject invention further concerns a novel means for introducing phytotoxin, disrupting nutrient flow, and inducing selective mortality for population control of a pest plant species.

5 Claims, No Drawings

USE OF MICROORGANISM TO PRODUCE TOXIN

CROSS-REFERENCE TO A RELATED APPLICATION

This is a continuation-in-part of co-pending application Ser. No. 07/278,685, filed Dec. 1, 1988, now abandoned.

BACKGROUND OF THE INVENTION

Beneficial uses of microorganisms are well known in the art and have been documented at great length. Many patents have issued which claim new microbial processes pertaining to the production of antibiotics, enzymes, ethanol, and a multitude of other useful products. Microorganisms are also used to clean up toxic wastes and oil spills, kill pests, recover minerals, and provide nutrients to plants. It has been known for many years that some organisms produce compounds which are toxic to other organisms. The production of the antimicrobial compound penicillin by penicillium mold is one such example.

Microorganisms are particularly attractive candidates for use in making and delivering organic compounds because they can be extremely efficient and safe. The modern tools of genetic engineering have greatly enhanced the ability to exploit the efficiency and relative safety of microbes. Even in the absence of genetic manipulation, however, microbes can perform highly specific tasks which make them indispensable in certain applications. Thus, there is a constant ongoing search in many areas of research for new microbes with specific advantageous properties. The subject invention concerns the discovery of one such microbe.

Weeds are a tremendous problem for farmers throughout the United States and the Caribbean region. Weeds cause a 10–12% loss of value for agricultural products in the United States, the most recent estimate being $20 billion annually (McWhorter, C. G. [1984] Weed Sci. 32:850–855). In Florida, vegetable production alone, losses due to weeds are estimated to be over $100 million. According to the most recent estimates, 41% of the cost of plant protection was for the control of weeds. Herbicides are applied to more acres than fungicides and insecticides combined. Weeds act as alternate hosts for insects, fungi, bacteria, and viruses. They affect man, not only by competing with crop plants, but by poisoning range animals, interfering with right-of-ways and roadways, decreasing forest production, and marring landscapes.

Nutsedges (Cyperus spp.) comprise a group of commonly occurring weeds that are among the most difficult to control. In the Caribbean Basin there are three species which are of most consequence, namely C. rotundus (purple nutsedge), C. esculentus (yellow nutsedge), and C. iria (rice flatsedge). Purple nutsedge has been called the world's worst weed because of its distribution worldwide and its resistance to control measures (Holm, L. G., D. L. Plucknett, J. V. Pancho, and J. P. Herberger [1977] *The World's Worst Weeds: Distribution and Biology*. University Press of Hawaii, Honolulu). It is a problem in 52 crops in more than 90 tropical and subtropical countries. It is considered a serious weed in the United States and a principal weed in Puerto Rico. Yield reduction due to nutsedge varies. In agronomic crops, yield reduction can be as high as 79%, as was seen in maize. In horticultural crops, yield reduction can reach 80%, as has been seen in beans. Yield reduction in tomato, a very valuable crop in the Caribbean region, can be as high as 53%. Nutsedges cannot compete with crops if a dense crop canopy is established, making early season control of these weeds essential.

In Florida, purple and yellow nutsedge, and rice flatsedge are problems in virtually every crop grown in the state. In Puerto Rico, the major problem is with purple nutsedge, although the other species are also found. Vegetables, particularly tomato, pumpkin, pepper, and onion, are affected. In the Virgin Islands the major species is also purple nutsedge which causes the greatest problems in vegetables. Purple nutsedge is also widely distributed in other crops throughout the Caribbean Basin.

Many herbicides have been tested for control of purple and yellow nutsedge. Pereira et al. recently reviewed this research (Pereira, W., G. Crabtree, and R. D. William [1987] Weed Technology 1:92–98). Herbicides based on virtually every mode of action have been studied. Examples are: 2,4-D ("control erratic"), atrazine ("control inconsistent"), linuron ("marginal control"), paraquat ("inconsistent"), alachlor and metolachlor ("control temporary"). Some herbicides that have been used successfully include glyphosate, dichlobenil, EPTC, arsenicals, and soil fumigants. Success or failure of a herbicide treatment depends on such factors as nutsedge growth stage at application, soil moisture and temperature, and addition of adjuvants to the spray mixture.

Chemical weed control programs are seriously inadequate for control of this weed. Frequently the weed germinates below the treated zone and avoids herbicide injury. Although many herbicides have been developed and tested in the last three decades, farmers still rely heavily on dinoseb, a herbicide developed in the 1950's. Dinoseb is a contact herbicide that causes injury to some field crops. Alternative approaches include monosodium methanearsonate (MSMA), paraquat, toxaphene, and triazine herbicides, but these chemicals are not registered for use on some crops for reasons of toxicology and/or crop safety.

The use of chemical pesticides in agriculture is currently a major concern in the U.S. Nowhere is this concern more obvious than in the San Joaquin Valley of California, where pesticides are being blamed for an epidemic of cancer in children and young adults (Weisskopf, M. [1988] The Washington Post Weekly Edition 5(47):10–11, Washington, D.C.). New technologies in detection methods are enabling researchers to find pesticides in the environment that were previously thought to be totally degraded. Perhaps the major public concern of the 1980's is protection of groundwater. The Environmental Protection Agency (EPA) estimates that 100,000 of the nation's 1.3 million wells are contaminated with pesticides (Fleming, M. H. [1987] Amer. J. Alternative Agriculture 2:124–130). This has alarmed the general public since 50% of all Americans depend on groundwater wells for their fresh water supplies. Because herbicides are so widely used in agriculture, and because they are often applied directly to the soil, the potential for movement into groundwater by leaching is perhaps greater than any other pesticide. Other inadequacies of chemical controls include lack of residual control, injury to non-target organisms, undesirable residues in harvested products, and carryover in subsequent crops.

There are no selective herbicides which can be used to control these sedges in all crops. Indeed, those herbicides which are available do not always give acceptable control of these weeds. An alternative is offered by the use of microbes which have herbicidal activity specific for the problem weeds, and do not infect desirable plants.

Phatak et al. (Phatak, S. C., M. B. Callaway, and C. S. Vavrina [1987] Weed Technology 1:84–91) have reviewed biological control of purple and yellow nutsedge. Cost effective procedures for the use of insects to control these species have not been developed. Phatak has reported that manipulation of a rust pathogen (*Puccinia canaliculata*) of yellow nutsedge has reduced stand, tuber formation, and completely inhibited flower formation of this weed. Phatak points out that little research has been directed toward integrating biological and chemical control of nutsedge. It was shown that rust-paraquat (1,1'-dimethyl-4,4'-bipyridinium ion) combinations were much more effective than either treatment alone. Other work indicates that sequential applications of the rust and other herbicides, such as bentazon[3-(1-methylethyl)-(1H)-2,1,3-benzothiadiazin-4-(3H)-one 2,2-dioxide] provided significantly better control than either applied alone. Although this system is promising, there are many aspects that must be investigated, such as spore production and maintenance in storage. Phatak also states that other pathogens should be sought to complement the rust system.

Therefore, the use of bioherbicides is becoming an increasingly important alternative to chemical herbicides. This importance is exemplified by several patents which have been issued for bioherbicides and their use. Some of these patents, by way of illustration, are as follows: U.S. Pat. No. 3,849,104 (control of northern jointvetch with *Colletotrichum gloeosporioides* Penz. *aeschynomene*); U.S. Pat. No. 3,999,973 (control of prickly sida [teaweed] and other weeds with *Colletotrichum malvarum*); U.S. Pat. No. 4,162,912 (control of milkweed vine with *Araujia mosaic* virus); U.S. Pat. No. 4,626,271 (Cyanobacterin Herbicide); and U.S. Pat. No. 4,915,726 (Biological Control of Dodder).

BRIEF SUMMARY OF THE INVENTION

The subject invention concerns a novel means for producing and delivering a toxin. Advantageously, the toxin produced according to the subject invention has been shown to have phytotoxic properties. The toxin is produced from novel fungal isolates. These novel isolates of the Curvularia and Fusarium genera can be grown, and the toxins recovered, by techniques which are well known to those skilled in the art.

Furthermore, it has been discovered that these fungi can be used to directly, and specifically, deliver their phytotoxin composition to nutsedges. Thus, in a preferred embodiment, the subject invention concerns the discovery of a novel method for control of nutsedges. This method has been shown to have surprising ability to provide specific control of both yellow and purple nutsedge. In this preferred embodiment, the phytotoxin composition of the subject invention is delivered to the nutsedge by applying an effective amount of the biologically-active fungus directly to the plant. The fungus produces sufficient quantities of a phytotoxic compound to inhibit the growth, or actually induce mortality, of the target weed. The growth of the fungus can also mechanically disrupt nutrient transport in the vascular system of the target weed.

The subject invention further concerns the novel microbes themselves, which are effective, when used according to the methods disclosed herein, in controlling yellow and purple nutsedge without adversely affecting the growth and yield of desired field crops. Preferably, the subject invention relates to the use of a composition comprising spores from novel Curvularia or Fusarium isolates in association with an agricultural carrier wherein said spores are in a concentration of from about $1 \times 10^4$ spores/ml of carrier to about $1 \times 10^9$ spores/ml of carrier. The concentrated spore formulation can be adapted for distribution over geographical locales or situs where the spores germinate and infect yellow or purple nutsedge.

DETAILED DESCRIPTION OF THE INVENTION

The subject invention provides a novel means of obtaining and using a toxin composition. This toxin composition is obtained from novel fungal isolates. Advantageously, the toxins produced by these fungal isolates have activity against nutsedge weeds, which are known to be particularly difficult to control. The toxins of the subject invention may also be purified and used against other weeds. For purposes of this application, a "weed" is any plant that is objectionable or interferes with the activities or welfare of man.

One highly useful aspect of the novel fungal isolates described herein is their unique and surprising ability to effectively and selectively deliver their toxin to nutsedges. Thus, an important aspect of the subject invention concerns a novel method for selective control of nutsedges.

Thus, the subject invention provides an effective species-specific means for controlling nutsedges. Specifically, a phytotoxin, or mixture of phytotoxins is delivered to the vascular tissue of these weeds. In a preferred embodiment of the subject invention, the spores or hyphae of the fungi Curvularia and/or Fusarium can be applied directly to the nutsedges. These fungi produce phytotoxins which control the nutsedges. These phytotoxins enter the vascular tissue of the nutsedge and cause foliar wilt and mortality. This effect can be enhanced by mechanical disruption of the plant's vascular system caused by the growth of the fungi.

One of the reasons mentioned for the success of nutsedges as invasive pest plant species was the apparent lack of mortality-inducing natural enemies. Nutsedges have not been reported previously in the literature to be colonized by microorganisms which effectively lead to death.

The use of these novel fungi to administer species-specific control of nutsedges is a highly advantageous means of reducing host populations. One of the primary advantages of using these effective microbial herbicides is the avoidance of pesticidal contamination of agricultural lands, waterways, and wetlands.

The phytotoxic composition of the subject invention can be delivered to the target pest by allowing Curvularia and/or Fusarium to grow directly on the weed. Advantageously, the phytotoxic composition is most effectively introduced onto the plant using standard agricultural carriers for this type of microbial herbicide.

The novel Fusarium described herein is the first fungal pathogen that has been used to successfully selectively control purple nutsedge. The Fusarium of the subject invention has been identified as *Fusarium oxysporum* Schlecht. The novel Curvularia described herein is the first fungal pathogen that has been used to successfully selectively control both yellow and purple nutsedge. The Curvularia of the subject invention has been identified as *Curvularia lunata* var. *aeria* (Wakker) Boedijn. The appearance and growth characteristics of these fungi would be known or easily ascertained by a person skilled in this art. There is no previous report of these fungi being pathogenic to nutsedges.

Subcultures of the novel fungi have been deposited in the permanent collection of the American Type Culture Collection (ATCC), 12301 Parklawn Drive, Rockville, Md. 20852 USA. The cultures were assigned the following accession numbers by the repository:

| Culture | Accession number | Deposit date |
|---|---|---|
| *Fusarium oxysporum* Schlecht | ATCC 20912 | November 29, 1988 |
| *Curvularia lunata* var. *aeria* | ATCC 74070 | June 18, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of a deposit. All restrictions on the availability to the public of the subject culture deposits will be irrevocably removed upon the granting of a patent disclosing them.

The pathogens of the subject invention can be grown on solid or in liquid media. Solid media that can be used include water agar, potato dextrose agar, V-8 agar, and string bean agar (strained extract of macerated string beans solidified in agar). Spores are produced on solid V-8 medium exposed to fluorescent light. Specifically, solid media can be, for example, (1) water agar, (2) potato dextrose agar (Difco), (3) lima bean agar (Difco), (4) corn meal agar (Difco), (5) potato-carrot agar (Tuite 19), and (6) Desmodium agar (blend 10 g Desmodium plant parts or plant extracts in 1000 ml water and solidify with 20 g agar).

For large scale production in fermentation tanks, liquid media is used, for example:

| Formula I - Modified Richard's Solution - V-8* | |
|---|---|
| Sucrose | 50 gm |
| Potassium nitrate | 10 gm |
| Potassium phosphate, monobasic | 5.0 gm |
| Magnesium sulfate.7H$_2$O | 2.50 gm |
| Ferric chloride | 0.02 gm |
| V-8 juice | 15 ml |
| Distilled water to make | 1000 ml |

*Trademark, The Campbell Soup Company for mixed vegetable juices.

Formula II—Modified Richard's Solution—Distillers Solubles—Same as Formula I but substitute 15 gm Distillers solubles for V-8 juice.

Formula III—Modified Richard's Solution—Brewers yeast—Same as Formula I above but substitute 15 gm brewers yeast for V-8 juice.

Formula IV—Modified Richard's Solution—Torula Yeast—Same as Formula I above but substitute 16 gm torula yeast for V-8 juice.

Formula V—Oatmeal solution—4%+2% sugar—
40 gm oatmeal
20 gm sucrose
1000 ml distilled water The preparation of spores is commenced in preseed liter flasks containing about 300 ml of liquid medium which have been inoculated with spores. The medium is incubated for 1-3 days with agitation at a temperature of about 26° C. to about 30° C.

The preseed is then transferred aseptically to 20 liter seek tanks with additional sterile medium as described above. The tanks are provided with sterile air and agitation. The cycle is continued at a temperature of about 26° C. to about 30° C. for 1 to 3 days.

Larger fermentors (250 liter) are aseptically inoculated with the seed tanks (entire contents), described above. Additional sterile medium, as used above, is added and the pH adjusted to about 6.0. The fermentor is supplied with sterile air and agitation, and is maintained at a temperature of about 26° C. to about 30° C. for from 1 to 3 days. The fermentor is then harvested by filtering the contents to remove insoluble solids and mycelia growth. The filtered beer is then centrifuged, the supernatant is discarded, and the remaining spore concentrate is collected, placed in plastic bags, and stored in ice. The concentrate so stored maintains an 80% germination for up to 21 days.

The spore concentrate is mixed with an agriculturally acceptable diluent or carrier for application to the undesired host vegetation or a situs. By the term "situs" is meant those areas infested with the undesired vegetation or potential infestation sites.

The preferred carrier is water, and the spore concentrate is dispersed to make a concentration of from about $2\times10^4$ to $2\times10^7$ spores/ml. The formulation is then sprayed on the undesired vegetation or situs by conventional spraying equipment in an amount of from about 50 to 500 liters per hectare.

Following are examples which illustrate procedures, including the best mode, for practicing the invention. These examples should not be construed as limiting. All percentages are by weight and all solvent mixture proportions are by volume unless otherwise noted.

EXAMPLE 1

Activity of Fusarium Isolate

The Fusarium of the subject invention was cultured in petri dishes containing standard potato dextrose agar (PDA). The spores were washed from the dishes with 10 ml of sterile distilled water, diluted with sterile distilled water, mixed with TWEEN 20 at 0.5% v/v, and applied to purple nutsedge plants raised from tubers in a greenhouse. The concentration of the suspension was $1.41 \times 10^6$ spores/ml as determined with a hemacytometer in the first experiment. The concentration was $4.5 \times 10^6$ spores/ml in the second experiment. The treated plants were placed in a dew chamber at 26° C. for 16 hours, then returned to the greenhouse for a two week incubation period. Control plants were treated with sterile distilled water containing 0.5% TWEEN 20 v/v, and given the same dew period and incubation conditions. Isolations were made from tissue showing lesions of any kind from both treatments. The tissue was surface sterilized by soaking in a 2.6% solution of sodium hypochlorite for 30 seconds. The tissue was subsequently rinsed in sterile distilled water for 30 seconds. The isolates were cultured on PDA. The fungi thus isolated were compared microscopically to the original isolate, and the results were compared with a comparison of binomials (Snedecor, G. W., and W. G. Cochran [1980] Statistical Methods. Iowa State Press, Ames, pp. 124-125). The following tables give the results of these tests. The results shown in Tables 1 through 3 indicate that this isolate is a pathogen of purple nutsedge.

TABLE 1

Results of experiment 1 testing the susceptibility of *Cyperus rotundus* to Fusarium sp.

| | Lesions sampled from treatment | | |
|---|---|---|---|
| | Treated with Fusarium | Control | Total |
| Fusarium not isolated | 20 | 25 | 45 |
| Fusarium isolated | 19 | 0 | 19 |
| Total | 39 | 25 | 64 |
| Proportion infected | 0.49 | 0.0 | 0.30 |

$Z = 4.15$
$P(Z \geq 4.15) < 3.17 \times 10^5$

TABLE 2

Results of experiment 2 testing the susceptibility of *Cyperus rotundus* to Fusarium sp.

| | Lesions sampled from treatment | | |
|---|---|---|---|
| | Treated with Fusarium | Control | Total |
| Fusarium not isolated | 11 | 21 | 32 |
| Fusarium isolated | 23 | 2 | 25 |
| Total | 34 | 23 | 57 |
| Proportion infected | 0.68 | 0.09 | 0.44 |

$Z = 4.40$
$P(Z \geq 4.40) < 3.17 \times 10^5$

TABLE 3

Combined results of two experiments testing the susceptibility of *Cyperus rotundus* to Fusarium sp.

| | Lesions sampled from treatment | | |
|---|---|---|---|
| | Treated with Fusarium | Control | Total |
| Fusarium not isolated | 31 | 46 | 77 |
| Fusarium isolated | 42 | 2 | 44 |
| Total | 73 | 48 | 121 |
| Proportion infected | 0.58 | 0.04 | 0.36 |

$Z = 6.01$
$P(Z \geq 6.01) < 2.87 \times 10^7$

EXAMPLE 2

Activity of Curvularia Isolate

Curvularia isolates were evaluated for pathogenicity on both sedge species. This was done using standard techniques: inoculum was produced on solid medium, conidia were washed from the cultures with sterilized distilled water, quantitated with a hemacytometer, adjusted to a known concentration, and suspended with a mild surfactant. Plants of both species were treated by spraying with an atomizer until runoff. Control plants were treated with sterilized distilled water containing the surfactant. After treatment the plants were placed in a dew chamber for 16 hours at 26° C. The plants were removed to a greenhouse where they were allowed to grow for 2 weeks. Samples were then taken from symptomatic tissue, and isolations were made from this tissue using sterile technique. The fungi isolated in this manner were compared to the original isolates. Results were compared with a comparison of binomials. The experiments were repeated in most cases and the results of the two experiments combined. Results of these experiments are shown in Tables 4 and 5.

During the tests outlined above, the Curvularia isolate was observed to cause death of plants of both species. In one case, about 40% of purple nutsedge plants died. For this reason, this isolate was selected for immediate further evaluation. Discs were cut from a culture growing on solid medium. The discs were placed on petri dishes, which were placed in a series of growth chambers in the dark. The growth chambers were set at the following temperatures: 0°, 5°, 10°, 15°, 20°, 25°, 30°, and 35° C. The radial growth of the cultures was determined for 9 days. At that time, the spores were washed from the plates with 10 ml of sterilized distilled water, and quantitated using a hemacytometer. The experiment was repeated. In this way, the effects of temperature on radial growth and sporulation could be determined. This experiment showed that the optimum temperature for growth was between 25° and 30° C., and the optimum temperature for sporulation was 30° C.

TABLE 4

Activity of Curvularia isolate against purple nutsedge.

| | Treatment | Control | Total |
|---|---|---|---|
| Infected | 107 | 2 | 109 |
| Clean | 99 | 108 | 207 |
| Total | 206 | 110 | 316 |
| P | 0.52 | 0.02 | 0.34 |

$Z = 8.93$
$P(Z \geq 8.93) < 2.87 \times 10^{-7}$

TABLE 5

Activity of Curvularia isolated against yellow nutsedge.

| | Treatment | Control | Total |
|---|---|---|---|
| Infected | 62 | 0 | 62 |
| Clean | 45 | 47 | 92 |
| Total | 107 | 47 | 154 |
| P | 0.58 | 0.00 | 0.40 |

$Z\ 6.7493$
$P(Z \geq 6.74) < 2.87 \times 10^{-7}$

EXAMPLE 3

Combinations of Herbicidal Agents

One embodiment of the subject invention concerns the combination of these isolates into a mycoherbicide for nutsedge control. Our novel fungal isolates can also be combined with the isolates of rust for control of yellow nutsedge. Spores of the novel fungi can also be mixed with spores of other bioherbicides to enlarge the scope of control of undersired vegetation. For example, a mixture of the novel Curvularia and/or Fusarium with *Alternaria cassiae* can be used to control both yellow and purple nutsedge and sicklepod (*Cassia obtusifolia*). Further, spores of the novel Curvularia and/or Fusarium can be mixed with those of *A. cassiae* to control yellow and purple nutsedge and showy crotalaria and coffee senna. The use of *A. cassiae* to control sicklepod, showy crotalaria or coffee senna is disclosed in U.S. Pat. No. 4,390,360, which is incorporated herein by reference thereto. The culture, means of growing, and application to these weeds disclosed in U.S. Pat. No. 4,390,360 can be used herein. Mixtures of Curvularia and *A. cassiae*, for example, *A. cassiae* NRRL 12533, can be made by methods well known in the art, utilizing the disclosure of U.S. Pat. No. 4,390,360, and that contained herein.

The novel Curvularia and/or Fusarium of the subject invention can also be mixed, in an agricultural carrier, with the rust pathogen *Puccinia canaliculata. P. canaliculata* has been reported to control yellow nutsedge and the mixture can be used to control both of these nutsedges. The novel Curvularia described here can also be mixed with *C. truncatum* (Schw.) Andrus & Moore, having the identifying characteristics of NRRL 15933, and is used to control Florida beggarweed as described in U.S. Pat. No. 4,693,756, issued to Cardina et al. This mixture could be used to control both purple nutsedge and Florida beggarweed.

The effectiveness of the novel Curvularia may also be enhanced by mixing it with chemical herbicides such as 2,4-D, atrazine, linuron, paraquat, alachlor, metolachlor, glyphosate, dichlobenil, EPTC, and arsenicals.

Table 6 provides a list of other groups of herbicides which could be used in conjunction with the novel fungus of the subject invention.

TABLE 6

| Herbicide group | Example |
|---|---|
| Carbamate | dichlobenil |
| Thiocarbamate | EPTC |
| Substituted urea | linuron |
| Triazine | atrazine |
| Asymmetrical triazine | metribuzin |
| Substituted uracil | terbacil |
| Chloroacetamide | metolachlor |
| Acid amide | pronamide |
| Bipyridinium | paraquat |
| Sulfonyl urea | chlorsulfuron |
| Imidazoinone | imazaquin |
| Dinitroaniline | trifluralin |
| Diphenyl ethers | oxyfluorfen |
| Difenoxycarboxylic acid | fluazifop |
| Benzoic acid | amiben |
| Phenoxy | 2,4-D |
| Unclassed | glyphosphate |

Though spores are the preferred form of the fungi, the fungi can also be used in their vegetative form. For example, fragmented mycelia can be formulated and applied to purple nutsedge in much the same manner as described above for the spore form.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A process for independently controlling yellow and purple nutsedge, said process comprising the application of a lethal amount of phytotoxin-producing fungus to said yellow or purple nutsedge or its situs, wherein said fungus is a *Curvularia lunata* var. *aeria*, ATCC 74070.

2. The process, according to claim 1, wherein said fungus is formulated with an appropriate agricultural carrier.

3. The process, according to claim 1, wherein said fungus is in the spore form at a concentration of from about $1\times10^4$ spores/ml of carrier to about $1\times10^9$ spores/ml of carrier.

4. A composition for agricultural application for controlling purple and yellow nutsedge comprising an isolate of the fungus *Curvularia lunata* var. *aeria*, ATCC 74070, in association with an agricultural carrier.

5. The composition, according to claim 4, wherein said Curvularia is in the spore form at a concentration of from about $1\times10^4$ spores/ml of carrier to about $1\times10^9$ spores/ml of carrier.

* * * * *

UNITED STATES PATENT AND TRADEMARK OFFICE
CERTIFICATE OF CORRECTION

PATENT NO. : 5,256,627
DATED : Oct. 26, 1993
INVENTOR(S) : Thomas A. Bewick

It is certified that error appears in the above-indentified patent and that said Letters Patent is hereby corrected as shown below:

Column 1     line 67: Delete "reduction" and insert --reductions--.

Column 8     line 49 (Table 5): Delete "isolated" and insert --isolate--.

Column 9     line 5: Delete "crotalaria and coffee" and insert --crotalaria or coffee--.

Column 9     line 7: Delete "crotalaria or coffee" and insert --crotalaria and coffee--.

Signed and Sealed this

Twelfth Day of April, 1994

Attest:

BRUCE LEHMAN

*Attesting Officer*     *Commissioner of Patents and Trademarks*